US009002430B2

(12) United States Patent
Riederer et al.

(10) Patent No.: US 9,002,430 B2
(45) Date of Patent: Apr. 7, 2015

(54) SYSTEM AND METHOD FOR COMBINED TIME-RESOLVED MAGNETIC RESONANCE ANGIOGRAPHY AND PERFUSION IMAGING

(75) Inventors: Stephen J Riederer, Rochester, MN (US); Norbert G Campeau, Rochester, MN (US); Clifton R Haider, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 10 days.

(21) Appl. No.: 13/520,302

(22) PCT Filed: Dec. 29, 2010

(86) PCT No.: PCT/US2010/062350
§ 371 (c)(1),
(2), (4) Date: Jul. 2, 2012

(87) PCT Pub. No.: WO2011/082225
PCT Pub. Date: Jul. 7, 2011

(65) Prior Publication Data
US 2013/0123611 A1 May 16, 2013

Related U.S. Application Data

(60) Provisional application No. 61/292,052, filed on Jan. 4, 2010.

(51) Int. Cl.
*A61B 5/05* (2006.01)
*A61B 5/026* (2006.01)
(Continued)

(52) U.S. Cl.
CPC .......... *A61B 5/0263* (2013.01); *G01R 33/4818* (2013.01); *G01R 33/5635* (2013.01); *G01R 33/56366* (2013.01); *G01R 33/4824* (2013.01)

(58) Field of Classification Search
CPC ............. A61B 5/0263; G01R 33/4818; G01R 33/56366; G01R 33/5635; G01R 33/4824
USPC .......................................................... 600/419
See application file for complete search history.

(56) References Cited

U.S. PATENT DOCUMENTS

2003/0045791 A1   3/2003  Carroll
2004/0044281 A1*  3/2004  Jesberger et al. ............. 600/419
(Continued)

OTHER PUBLICATIONS

Haider et al., 3D High Temporal and Spatial Resolution Contrast-Enhanced MR Angiography of the Whole Brain, Magn Reson Med. Sep. 2008; 60(3): 749-760.*
(Continued)

*Primary Examiner* — Long V Le
*Assistant Examiner* — Bo J Peng
(74) *Attorney, Agent, or Firm* — Quarles & Brady, LLP

(57) ABSTRACT

A method for performing magnetic resonance angiography and perfusion imaging using the same pulse sequence is provided. Time-resolved image data is acquired as a contrast agent passes through a subject. This image data is acquired by sampling Cartesian points in k-space that are contained within either a central region of k-space, or one of a plurality of different sets of radial sectors extending outwards from the central region. The image data is combined to form individual image frame data sets that are then reconstructed to produce a time series of image frames. From this time series, MR angiograms and perfusion maps are produced. With the added acquisition of calibration data, T1 relaxation parameters are estimated and quantitative perfusion maps produced.

20 Claims, 8 Drawing Sheets

(51) Int. Cl.
*G01R 33/48* (2006.01)
*G01R 33/563* (2006.01)

(56) References Cited

U.S. PATENT DOCUMENTS

2008/0061779 A1    3/2008   Feiweier
2008/0119720 A1*   5/2008   Carroll et al. ............ 600/410
2009/0238430 A1    9/2009   Haider et al.

OTHER PUBLICATIONS

Laub et al., formasyngo TWIST for Dynamic Time-Resolved MR Angiography, MAGNETOM FLASH Mar. 2006.*

Zheng et al., Combined MR Proton Lung Perfusion/Angiography and Helium Ventilation: Potential for Detecting Pulmonary Emboli and Ventilation Defects, Magn Reson Med. Mar. 2002; 47(3): 433-438.*

Goyen, Gadofosveset-enhanced magnetic resonance angiography, Vascular Health and Risk Management 2008:4(1) 1-9.*

Pipe et al. "Effects of Interleaf Order for Spiral MRI of Dynamic Processes." Magnetic Resonance in Medicine 41:417-422 (1999); pp. 417-418.

International Search Report and Written Opinion under date of Mar. 22, 2011 in connection with PCT/US2010/062350.

* cited by examiner

SYSTEM AND METHOD FOR COMBINED TIME-RESOLVED MAGNETIC RESONANCE ANGIOGRAPHY AND PERFUSION IMAGING

CROSS-REFERENCE TO RELATED APPLICATIONS

This application claims the benefit of PCT International Patent Application PCT/US2010/062350 filed Dec. 29, 2010 and U.S. Provisional patent application Ser. No. 61/292,052 filed on Jan. 4, 2010, and entitled "METHOD FOR COMBINED TIME-RESOLVED MAGNETIC RESONANCE ANGIOGRAPHY AND PERFUSION IMAGING", both of which are fully incorporated herein by reference in their entirety.

STATEMENT REGARDING FEDERALLY SPONSORED RESEARCH

This invention was made with government support under EB000212 awarded by the National Institute of Biomedical Imaging and Bioengineering. The government has certain rights in the invention.

BACKGROUND OF THE INVENTION

The present invention relates generally to magnetic resonance imaging ("MRI") systems and methods and, more particularly, the invention relates to systems and methods for magnetic resonance angiography ("MRA") and perfusion imaging.

When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically-proven pulse sequences and they also enable the development of new pulse sequences.

The MR signals acquired with an MRI system are signal samples of the subject of the examination in Fourier space, or what is often referred to in the art as "k-space." Each MR measurement cycle, or pulse sequence, typically samples a portion of k-space along a sampling trajectory characteristic of that pulse sequence. Many pulse sequences sample k-space in a raster scan-like pattern sometimes referred to as a "spin-warp," a "Fourier," a "rectilinear," or a "Cartesian" scan. The spin-warp scan technique employs a variable amplitude phase encoding magnetic field gradient pulse prior to the acquisition of MR spin-echo signals to phase encode spatial information in the direction of this gradient. In a two-dimensional implementation ("2DFT"), for example, spatial information is encoded in one direction by applying a phase encoding gradient, $G_y$, along that direction, and then a spin-echo signal is acquired in the presence of a readout magnetic field gradient, $G_x$, in a direction orthogonal to the phase encoding direction. The readout gradient present during the spin-echo acquisition encodes spatial information in the orthogonal direction. In a typical 2DFT pulse sequence, the magnitude of the phase encoding gradient pulse, $G_y$, is incremented, $\Delta G_y$, in the sequence of measurement cycles, or "views" that are acquired during the scan to produce a set of k-space MR data from which an entire image can be reconstructed.

There are many other k-space sampling patterns used by MRI systems. These include "radial," or "projection reconstruction" scans in which k-space is sampled as a set of radial sampling trajectories extending from the center of k-space. The pulse sequences for a radial scan are characterized by the lack of a phase encoding gradient and the presence of a readout gradient that changes direction from one pulse sequence view to the next. There are also many k-space sampling methods that are closely related to the radial scan and that sample along a curved k-space sampling trajectory rather than the straight line radial trajectory.

An image is reconstructed from the acquired k-space data by transforming the k-space data set to an image space data set. There are many different methods for performing this task and the method used is often determined by the technique used to acquire the k-space data. With a Cartesian grid of k-space data that results from a 2D or 3D spin-warp acquisition, for example, the most common reconstruction method used is an inverse Fourier transformation ("2DFT" or "3DFT") along each of the 2 or 3 axes of the data set. With a radial k-space data set and its variations, the most common reconstruction method includes "regridding" the k-space samples to create a Cartesian grid of k-space samples and then performing a 2DFT or 3DFT on the regridded k-space data set. In the alternative, a radial k-space data set can also be transformed to Radon space by performing a 1DFT of each radial projection view and then transforming the Radon space data set to image space by performing a filtered backprojection.

Magnetic resonance angiography ("MRA") uses the magnetic resonance phenomenon to produce images of the human vasculature. To enhance the diagnostic capability of MRA a contrast agent such as gadolinium can be injected into the patient prior to the MRA scan. Typically, one of the tricks with this contrast enhanced ("CE") MRA method is to acquire the central k-space views at the moment the bolus of contrast agent is flowing through the vasculature of interest. Collection of the central lines of k-space during peak arterial enhancement is key to the success of a CE-MRA exam. If the central lines of k-space are acquired prior to the arrival of contrast, severe image artifacts can limit the diagnostic information in the image. Alternatively, arterial images acquired after the passage of the peak arterial contrast are sometimes obscured by the enhancement of veins. In many anatomic regions, such as the carotid or renal arteries, the separation between arterial and venous enhancement can be as short as 6 seconds.

The short separation time between arterial and venous enhancement dictates the use of acquisition sequences of either low spatial resolution or very short repetition times ("TR"). Short TR acquisition sequences severely limit the signal-to-noise ratio ("SNR") of the acquired images relative to those exams in which longer TRs are possible. The rapid acquisitions required by first pass CE-MRA methods thus impose an upper limit on either spatial or temporal resolution.

As indicated above, the acquisition of MRA data is timed such that the central region of k-space is acquired as the bolus of contrast agent arrives in the arteries of interest. The ability to time the arrival of contrast varies considerably and it is helpful in many applications where proper timing is difficult to acquire a series of MRA image frames in a dynamic study that depicts the separate enhancement of arteries and veins. Such temporal series of image frames is also useful for observing delayed vessel filling patterns caused by disease. This requirement has been partially addressed by acquiring a series of time resolved images using a 3D "Fourier" acquisition. When a dynamic study is performed the time resolution of the study is determined by how fast the k-space data can be acquired for each image frame. This time resolution objective is often compromised in order to acquire all the k-space data needed to produce image frames of a prescribed resolution without undersampling artifacts.

Perfusion imaging is employed to assess the viability of tissues. An exemplary perfusion imaging method includes administering a contrast agent to the subject, after which a series of MR images are acquired as the contrast agent perfuses into the tissues of interest. From this series of contrast-enhanced MR images hemodynamic parameters such as blood flow, blood volume and mean transit time may be computed.

Hemodynamically weighted MR perfusion images of cerebral blood flow ("CBF") may be acquired and used in combination with diffusion-weighted ("DWI") MR images to delineate regions of viable brain parenchyma that are at risk of further infarction. The DWI MR image shows ischemic regions where brain cells have died, and the CBF image shows regions with reduced blood flow that indicates at risk tissue. The size of the "ischemic penumbra" surrounding ischemic tissues is a critical component in evaluating treatment options.

It is possible to assess regional cerebral hemodynamics by analyzing MR signal intensity changes after the first pass of the paramagnetic contrast medium. While passing through the capillary network, a short bolus of contrast material produces local magnetic field inhomogeneities that lead to a reduction in the transverse magnetization relaxation time $T_2^*$ of the bulk tissue. This susceptibility effect can be recorded by a series of rapid $T_2^*$-weighted gradient echo images that reveal how the MR signal changes during the first pass of the contrast agent. The resulting MR signal intensity versus time curves can be converted into contrast agent concentration-time curves. By using the indicator dilution theory, two important hemodynamic parameters can be determined from these curves: the CBF, known as tissue perfusion, and the cerebral blood volume ("CBV"). However, the concentration of contrast agent in the arterial blood pool, the so-called "arterial input function" ("AIF"), must be known if absolute quantification of the CBV and CBF measurements are to be achieved. Typical methods used to measure the AIF require a step in which the operator manually selects a region of interest ("ROI"), based on anatomic information, that depicts an artery. The concentration-time curve from all voxels included in the ROI is then used to calculate the AIF.

Given the clinical usefulness of both MRA images and MR perfusion images, some have attempted to combine the acquisition of the information for both image types. For example, some have combined dynamic contrast-enhanced (DCE) MRI perfusion images with MRA images in a serial fashion.

Of course, as addressed above, CE-MRA imaging presents the need to time the passage of the peak arterial contrast and maintain a separation between arterial and venous enhancement. In a serial perfusion and MRA acquisition, performing perfusion imaging before the CE-MRA data acquisition leads to unwanted venous contamination in the subsequent time-resolved MRA image. On the other hand, performing the time-resolved MRA before perfusion imaging confounds the subsequent perfusion study because the baseline background signal is enhanced.

Accordingly, some have proposed interleaving segments of a 3D MRA data acquisition with multiple complete 2D perfusion image data acquisitions. To make such a combination of two separate pulse sequence more tolerable, some proposed collecting few phase-encoding lines and shortening the TR of the 2D perfusion data acquisitions. However, doing so lowers the overall data acquisition time by reducing the resolution of the acquired perfusion images. Similarly, attempts to sacrifice the temporal resolution of the perfusion and/or MRA images to control the duration of the overall data acquisition time are limited, for example, at least by the speed and timing of the contrast enhancement. In any case, even when clinical needs can tolerate substantial sacrifices in spatial or temporal resolution of the resulting images, these interleaving methods inevitably increase the acquisition times and can present substantial challenges in coordinating contrast passage during imaging acquisition and tolerating less-than-ideal contrast enhancement.

Therefore it would be desirable to have a system and method for acquiring angiographic and perfusion images using MRI in a coordinated fashion that does not unduly extend acquisition times or require particular data to be acquired during periods timed to undesirable phases of contrast enhancement for the data to be acquired.

SUMMARY OF THE INVENTION

The present invention overcomes the aforementioned drawbacks by providing a system and method for providing both angiographic and perfusion information using a single MRI acquisition by acquiring MR data in a Cartesian acquisition that samples k-space in a manner that, at a distance, has features similar to projection reconstruction sampling of k-space. From the data acquired in this k-space sampling strategy, a plurality of image-frame data sets is assembled and a time-series of images frames is reconstructed therefrom. An MRA image and a perfusion image is produced using the time-series of images frames.

In accordance with the present invention, the present invention divides k-space into a central region of k-space and a plurality of radially-extending k-space sectors that extend outward from the central region of k-space to an outer boundary of k-space. Sampling of k-space is performed by sampling locations within the central region of k-space during a first period and sampling locations within a plurality of the radially-extending k-space sectors during a second period. This k-space sampling during the first and second period is repeated a plurality of times in order to acquire time-resolved image data. A plurality of image-frame data sets are then formed by combining data acquired from the first period with data acquired during the second period. A time series of images is reconstructed from the image frame data sets and, therefrom, an MRA image and perfusion image are produced.

In accordance with another aspect of the present invention, a method for producing a magnetic resonance angiography ("MRA") image and a perfusion image of a subject with a magnetic resonance imaging ("MRI") system is provided.

After a contrast agent is administered to the subject, the MRI system is used to acquire image data. Image data is acquired by performing a pulse sequence that samples locations in k-space within a central region of k-space during a first time frame and locations in k-space within a plurality of different sets of radial k-space sectors during a respective plurality of additional time frames. These radial sectors extend outward from the central region of k-space to an outer boundary of k-space. This process is repeated a plurality of times to acquire time-resolved image data. A plurality of image-frame data sets is then formed by combining time-resolved image data acquired by sampling the central region of k-space with time-resolved image data acquired by sampling a variety of the different sets of radial k-space sectors. From these image frame data sets, a time series of image frames is reconstructed. These images are then used to produce an MRA image and perfusion image of the subject.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
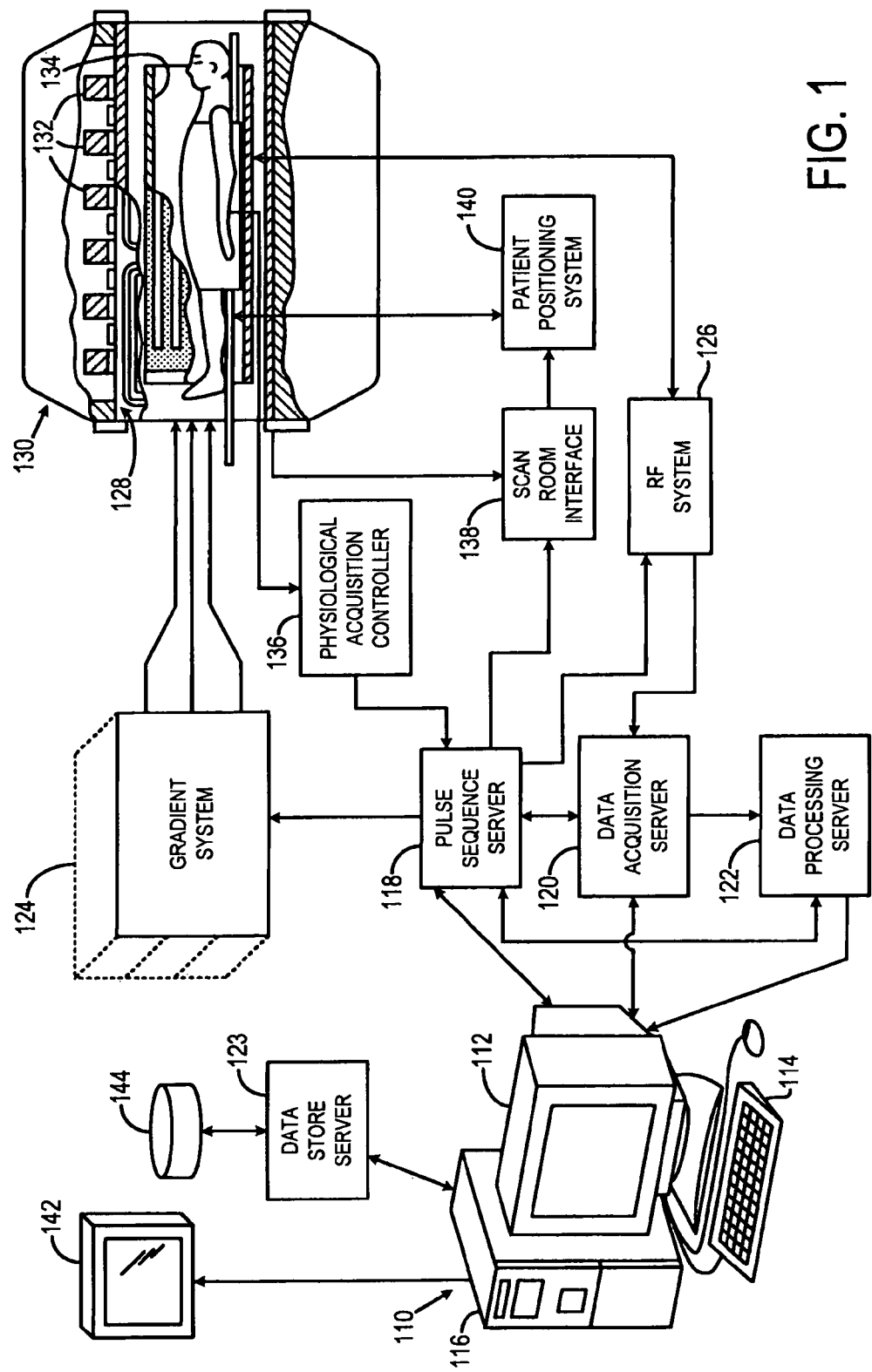
FIG. 1 is a block diagram of an MRI system that employs the present invention.

Referring particularly to FIG. 1, the invention is employed in a magnetic resonance imaging ("MRI") system. The MRI system includes a workstation 110 having a display 112 and a keyboard 114. The workstation 110 includes a processor 116 that is a commercially available programmable machine running a commercially available operating system. The workstation 110 provides the operator interface that enables scan prescriptions to be entered into the MRI system. The workstation 110 is coupled to four servers: a pulse sequence server 118; a data acquisition server 120; a data processing server 122, and a data store server 123. The workstation 110 and each server 118, 120, 122 and 123 are connected to communicate with each other.

The pulse sequence server 118 functions in response to instructions downloaded from the workstation 110 to operate a gradient system 124 and a radiofrequency ("RF") system 126. Gradient waveforms necessary to perform the prescribed scan are produced and applied to the gradient system 124 that excites gradient coils in an assembly 128 to produce the magnetic field gradients $G_x$, $G_y$, and $G_z$ used for position encoding MR signals. The gradient coil assembly 128 forms part of a magnet assembly 130 that includes a polarizing magnet 132 and a whole-body RF coil 134.

RF excitation waveforms are applied to the RF coil 134 by the RF system 126 to perform the prescribed magnetic resonance pulse sequence. Responsive MR signals detected by the RF coil 134 or a separate local coil (not shown in FIG. 1) are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays (not shown in FIG. 1).

The RF system 126 also includes one or more RF receiver channels. Each RF receiver channel includes an RF amplifier that, amplifies the MR signal received by the coil to which it is connected and a detector that detects and digitizes the I and Q quadrature components of the received MR signal. The magnitude (M) of the received MR signal may thus be determined at any sampled point by the square root of the sum of the squares of the I and Q components:

$$M = \sqrt{I^2 + Q^2},$$

and the phase of the received MR signal may also be determined:

$$\phi = \tan^{-1}\left(\frac{Q}{I}\right).$$

The pulse sequence server 118 also optionally receives patient data from a physiological acquisition controller 136. The controller 136 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 138 that receives signals from various sensors associated with the condition of the patient and the magnet system. It is also through the scan room interface circuit 138 that a patient positioning system 140 receives commands to move the patient to desired positions during the scan.

The digitized MR signal samples produced by the RF system 126 are received by the data acquisition server 120. The data acquisition server 120 operates in response to instructions downloaded from the workstation 110 to receive the real-time MR data and provide buffer storage such that no data is lost by data overrun. In some scans the data acquisition server 120 does little more than pass the acquired MR data to the data processor server 122. However, in scans that require information derived from acquired MR data to control the further performance of the scan, the data acquisition server 120 is programmed to produce such information and convey it to the pulse sequence server 118. For example, during prescans MR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process MR signals used to detect the arrival of contrast agent in a magnetic resonance angiography (MRA) scan. In all these examples the data acquisition server 120 acquires MR data and processes it in real-time to produce information that is used to control the scan.

The data processing server 122 receives MR data from the data acquisition server 120 and processes it in accordance with instructions downloaded from the workstation 110. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 122 are conveyed back to the workstation 110 where they are stored. Real-time images are stored in a data base memory cache (not shown) from which they may be output to operator display 112 or a display 142 that is located near the magnet assembly 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

Figure 2:
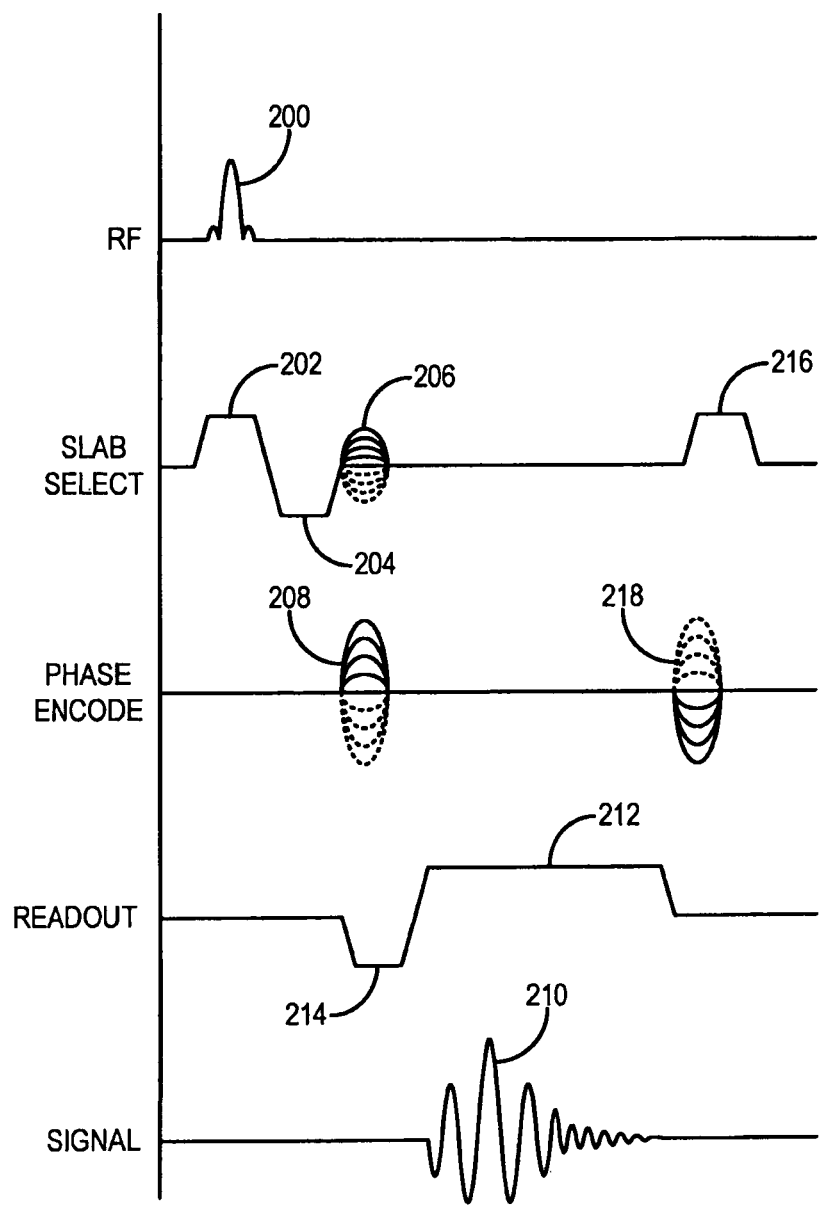
FIG. 2 is a graphic illustration of an exemplary 3D spoiled gradient recalled echo pulse sequence employed when practicing some aspects of the present invention.

Referring now to FIG. 2, an exemplary 3D spoiled gradient echo pulse sequence that is employed when practicing the present invention is illustrated. The pulse sequence begins with the selective excitation of a region-of-interest ("ROI") with a radio frequency ("RF") excitation pulse 200 in the presence of a slab selective gradient pulse 202. The frequency content of the excitation pulse 200 and the amplitude of the slab selective gradient pulse 202 are selected to produce transverse magnetization in the ROI that is the subject of the scan. The slab selective gradient pulse 202 concludes with a negative gradient lobe 204 that is played out to rephase the excited spins in preparation for phase encoding and readout.

Phase encoding is performed along two axes, for example, the y-axis and the z-axis. The z-axis encoding is accomplished by applying a phase encoding pulse 206 along the $G_z$ gradient axis and the y-axis encoding is accomplished by applying a phase encoding pulse 208 along the $G_y$ gradient axis. As is well-known to those skilled in the art, the magnitude of the phase encoding pulses 206 and 208 are stepped through a series of positive and negative values during the scan, but each is set to one value during each repetition of the pulse sequence. As will be described in detail below, the order in which these phase encoding pulses, 206 and 208, are stepped through their set of values will depend on the particular clinical application of the invention. As is well-known in the art, the magnitude of a phase encoding gradient pulse is determined by the integral of its amplitude over its duration, that is, its area. In most pulse sequences the duration is kept constant and the phase encoding pulse magnitude is stepped through its values by changing its amplitude.

After phase encoding the transverse magnetization, an MR echo signal 210 is read out in the presence of a readout gradient 212. This readout is preceded by a negative gradient lobe 214 in order to produce a gradient refocused echo signal 210 in the usual fashion. The pulse sequence is then concluded by the application of a large spoiler gradient pulse 216 and a rewinder gradient pulse 218 to prepare the magnetization for the next repetition of the pulse sequence, which follows thereafter. As is known to those skilled in the art, the spoiler gradient pulse 216 dephases transverse magnetization and the rewinder pulse 218 refocuses transverse magnetization along the applied axis in preparation for the next pulse sequence. Moreover, the rewinder pulse 218 is equal in magnitude, but opposite in polarity with the phase encoding pulse 208. In the alternative, RF spoiling may be used to dephase the transverse magnetization.

The acquisition of data in 3DFT scanning can be considered sampling of a three-dimensional "k-space." Two of the dimensions, $k_y$ and $k_z$, are sampled by applying the different phase encoding gradients 208 and 206, respectively, during each repetition of the pulse sequence, and each acquired echo signal 210 contains, for example, 256 samples along a line in the $k_x$ direction. The pulse sequence is repeated for as many repetitions as are necessary to sample all desired $k_y$ and $k_z$ values. For example, $k_y$ may assume 128 different values and $k_z$ may have 64 values. In such a case, the number of repetitions of the pulse sequence would be 128×64, or 8192.

Figure 3:
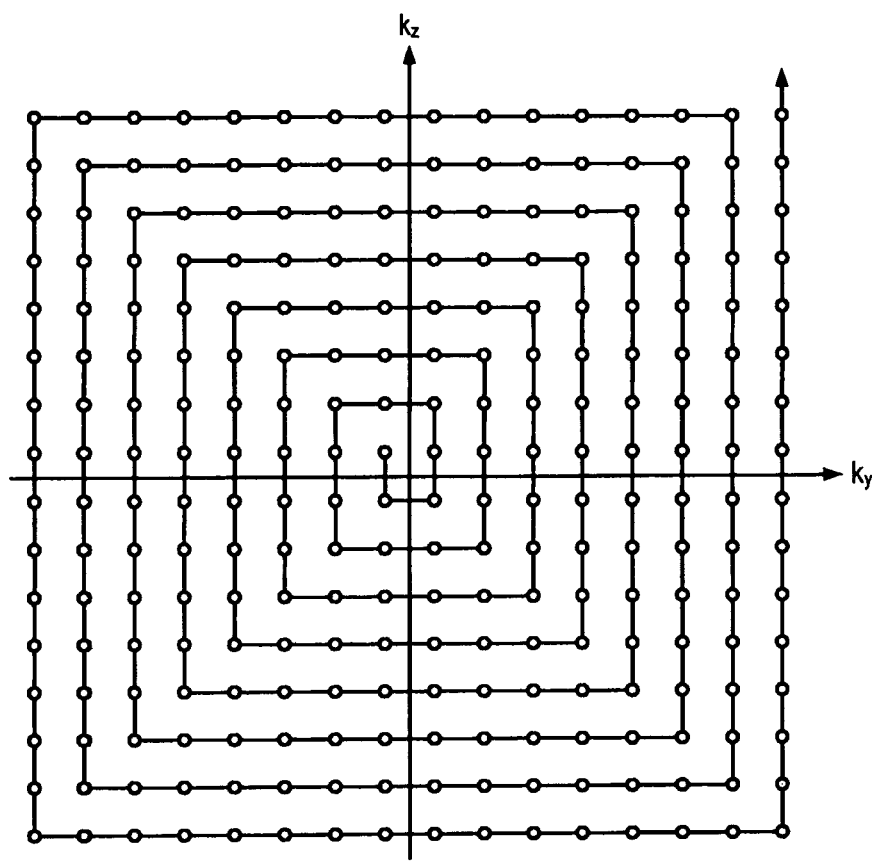
FIG. 3 is a graphic illustration of an exemplary square spiral centric view order sampling pattern in k-space.

Centric view ordering is based on the realization that, for most objects, the bulk of the signal power is contained in the samples acquired near the origin of k-space. Thus, it follows that it is these samples that contribute most significantly to the appearance of the reconstructed image. This results from the fact that the NMR signals acquired during the scan are Fourier transformed along the $k_x$, $k_y$, and $k_z$ directions to produce intensity values for an image in real (x, y, z), or "image," space. By way of example, the succeeding discussion is presented with respect to sampling the $k_y$-$k_z$ plane using centric view ordering. However, this is only an example. It is the nature of this transformation, then, that the samples acquired near the k-space origin ($k_y$=0, $k_z$=0) contribute a disproportionate share to the signal power of the reconstructed image. Accordingly, it is a basic idea of centric view ordering to sample the ($k_y$,$k_z$) points that contain the most signal power in as short a time and as close to the beginning of the scan as possible. This can be done by modifying the k-space trajectory along which the $k_y$-$k_z$ plane is sampled. For example, a square spiral trajectory, such as the one shown in FIG. 3 may be used. With such a trajectory, the scan starts at or near the origin of the $k_y$-$k_z$ plane and progressively works its way outward in a spiral fashion. The manner in which the values of the $G_y$ and $G_z$ phase encoding gradients, 208 and 206, respectively, may be stepped to accomplish such a square spiral trajectory is described, for example, in U.S. Pat. No. 5,122,747, which is incorporated herein by reference.

In accordance with some aspects of the invention, another centric view order scheme, the so-called "elliptical centric" ("EC") view order, such as the one described, for example, in U.S. Pat. No. 5,912,557 and incorporated herein by reference, may be utilized. This is a view order based on the distance of the sample point from the origin of k-space. By way of example, it is assumed that the field-of-view along the y-axis is the quantity "FOV" and that the field-of-view along the z-axis is some fraction of this, FOV/N. The $k_y$ values that are to be sampled in the phase encoding process are:

$$\pm \frac{1}{(2 \cdot FOV)}, \pm \frac{3}{(2 \cdot FOV)}, \pm \frac{5}{(2 \cdot FOV)}, \cdots, \pm \frac{m}{(2 \cdot FOV)}; \quad \text{Eqn. (1)}$$

where m+1 is the total number of $k_y$ phase encodes desired. This assumes that the $k_y$ origin is not sampled and that the smallest nonzero $k_y$ spatial frequencies sampled are at 1/(2 FOV). Similarly, the $k_z$ values that are to be sampled are:

$$\pm \frac{N}{(2 \cdot FOV)}, \pm \frac{3 \cdot N}{(2 \cdot FOV)}, \pm \frac{5 \cdot N}{(2 \cdot FOV)}, \cdots, \pm \frac{n \cdot N}{(2 \cdot FOV)}; \quad \text{Eqn. (2)}$$

where n+2 is the total number of $k_z$ phase encodes. All phase encodings to be sampled can then be characterized by the index (i,j), where:

$-m \leq i \leq m$ and $-s \leq j \leq n$; and the index values i and j assume nonzero integer values. The distance from the k-space origin to a sample point is characterized by the indices (i,j), and is equal to:

$$\frac{1}{FOV} \cdot \sqrt{(2|i|-1)^2 + N^2(2|j|-1)^2} . \quad \text{Eqn. (3)}$$

Once the distance is determined for the k-space sample points (i,j), the points are ranked on the basis of their respective distances with the point having the smallest distance being ranked first. In this way, the ordered list of desired phase encodings, or views, is determined and stored for use during a scan in which image data is acquired.

Figure 4:
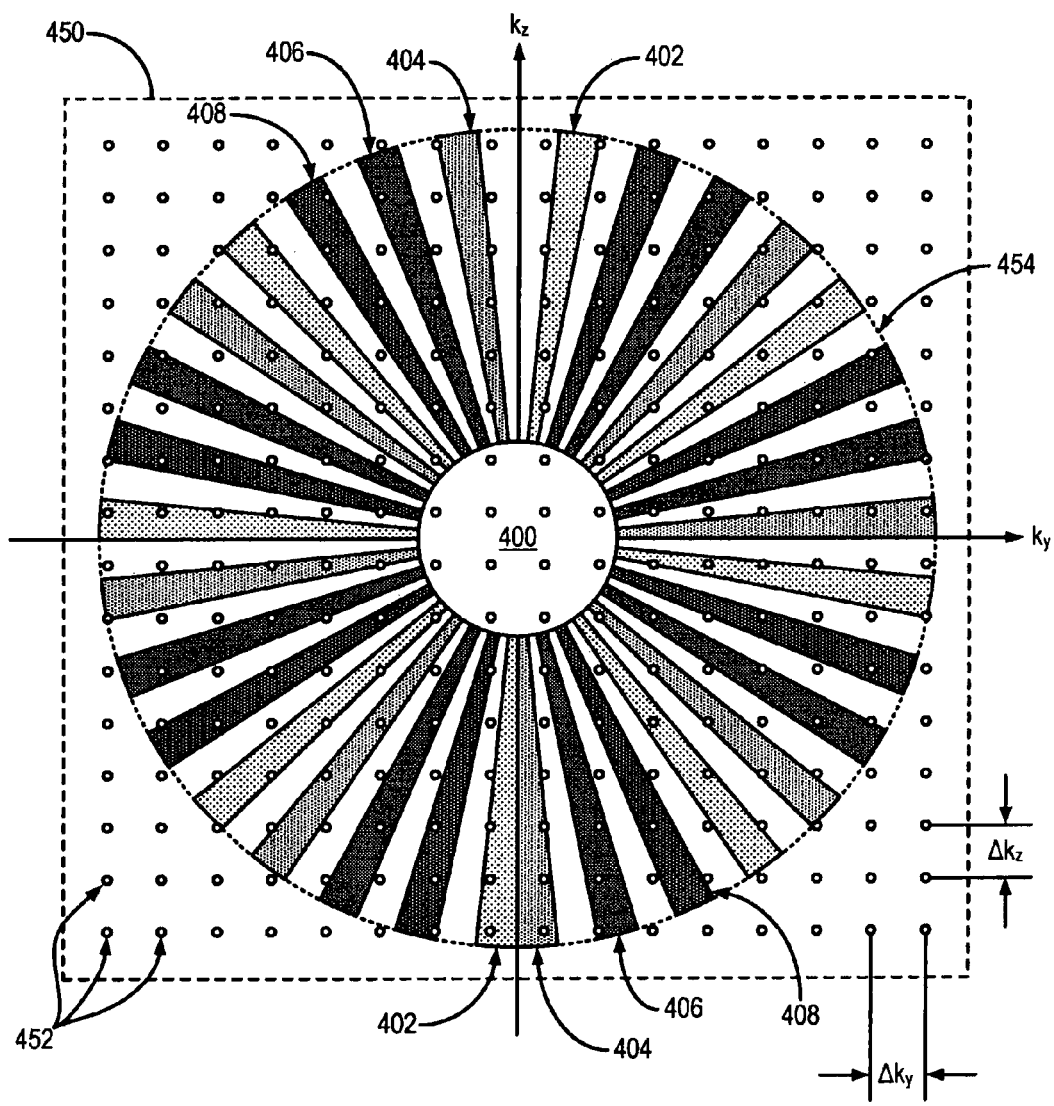
FIG. 4 is a graphic illustration of an exemplary sampling pattern employed when practicing some aspects of the present invention.

Referring particularly to FIG. 4, the present invention may employ a prescribed k-space sampling pattern that utilizes elliptical centric view order to sample a central region 400 of, for example, $k_y$-$k_z$ space. The prescribed field-of-view and resolution of the desired image dictates that $k_y$-$k_z$ space be bounded by rectangle 450 and be sampled at the grid of sample points, indicated by circles 452, for full k-space sampling. However, this k-space is only partially sampled. Substantially full sampling is done in the central region 400 and only partial sampling is done in the peripheral, annular portion of $k_y$-$k_z$ space, as indicated by the sets of darkened radial sectors 402, 404, 406, and 408 that extend radially outward from the central region 400. In particular, four different sets of radial sectors (402, 404, 406, and 408) are utilized to sample the peripheral region of $k_y$-$k_z$. As will be described below in detail, the image data acquired using different sets of radial sectors can be combined to reconstruct an image of the subject. The periphery of the sampled $k_y$-$k_z$ space is defined by an ellipse whose dimensions are determined by $k_{y,max}$ and $k_{z,max}$. The central region 400 occupies, for example, 10-20 percent of k-space, and the sampled radial sectors (402, 404, 406, and 408) sample, for example, 50 percent of k-space within an outer boundary 454 of the peripheral, annular region of $k_y$-$k_z$ space. There is no k-space sampling beyond the outer boundary 454.

The sampled radial sectors 402, 404, 406, and 408 are conjugates of corresponding unsampled sectors of k-space. For example, a radial sector that samples positive $k_y$ locations and negative $k_z$ locations has a corresponding conjugate sector that is the symmetrical reflection of the radial sector about the origin that is unsampled. The sampled radial sectors (402, 404, 406, and 408) are, therefore, asymmetrical. The location and order that the central region 400 and radial sectors (402, 404, 406, and 408) are sampled is stored in a k-space sampling table. While a particular sampling order is preferred for this particular clinical application, it will be apparent to those skilled in the art that other sampling schemes may be preferred for other clinical applications and stored in the sampling table. For example, the radial sectors 402, 404, 406, and 408 can be arranged into a different number of groups other than the four illustrated in FIG. 4. Such changes to the sampling scheme serve to trade off frame rate with image quality. For example, if the radial sectors (402, 404, 406, and 408) are decomposed into eight groups of four sectors each instead of four groups of eight sectors each, as illustrated in FIG. 4, then the acquisition time per sector group is reduced and the time between consecutive image frames is smaller. However, when using this scheme, the time required to acquire the eight groups is longer than when the four groups are acquired. Moreover, there is an increased potential for undersampling artifacts with such a data acquisition scheme. As a result of these considerations, changes to the sampling scheme serve as a trade off between frame rate and image quality.

The sampling pattern illustrated in FIG. 4 is exemplary of an accelerated acquisition with R=2 along each of the phase encoding axes. That is to say, the sampling pattern includes a two-fold increase in the sampling intervals $\Delta k_y$ and $\Delta k_z$ compared to a sampling grid that satisfies the Nyquist criterion, such as the sampling intervals in the alternate sampling pattern illustrated in FIG. 5. The k-space sampling pattern is unchanged from that shown in FIG. 4; however, the sampling density is increased throughout the pattern of sample points 452.

Modifications can be made to accommodate more sampling points if it is desired to offset some of the SNR loss experienced when undersampling techniques are employed, or if higher spatial resolution is desired. The additional sample points may be used to enlarge the fully sampled central region 400, or they can be distributed to the outer k-space annulus to widen several sectors (402, 404, 406, and 408) and provide additional high-spatial frequency information, or they may be utilized to extend the outer boundary 454 of the k-space sampling pattern. In one embodiment, 58 percent of the sample points may be acquired during the scan.

Figure 5:
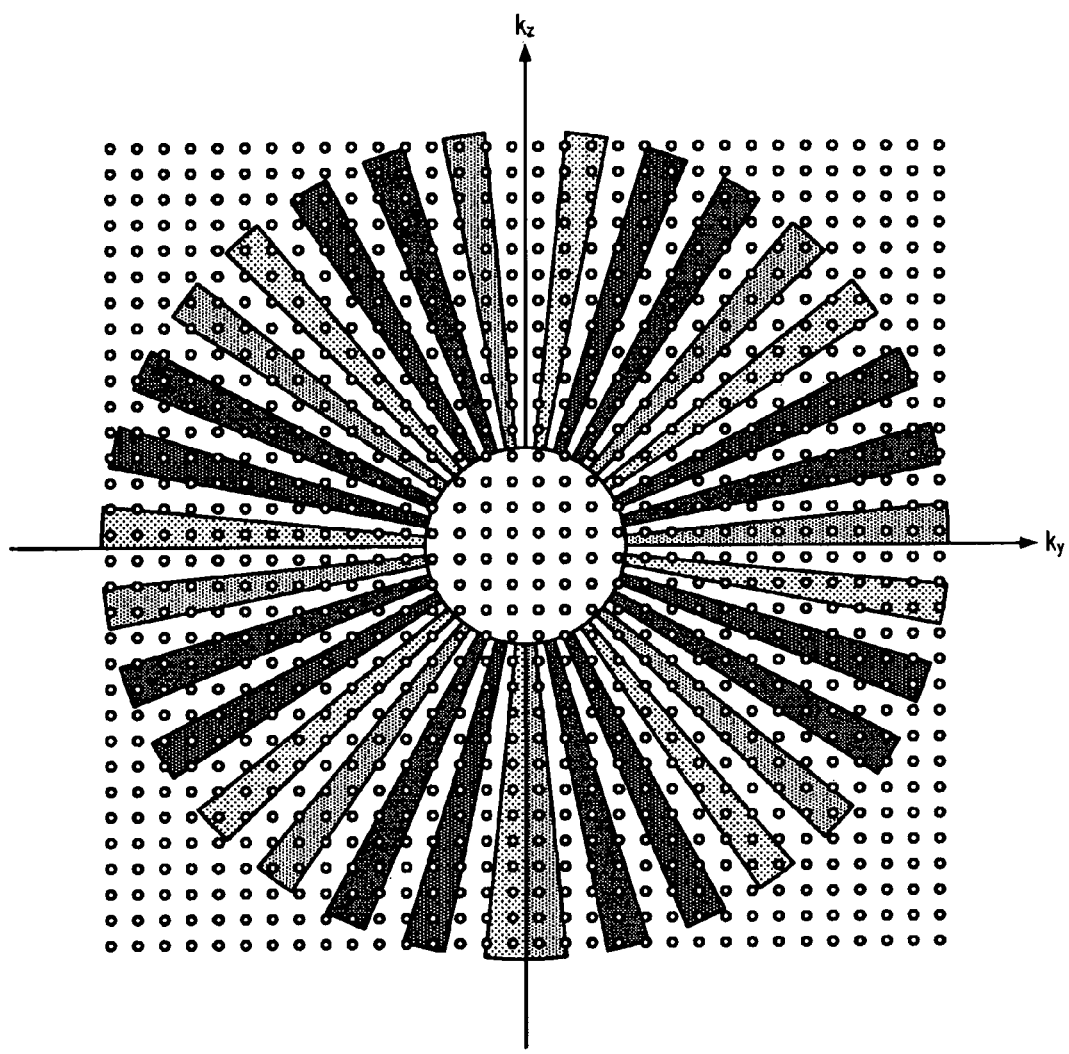
FIG. 5 is a graphic illustration of another exemplary sampling pattern employed when practicing some aspects of the present invention.

A 3D time-resolved technique employs the sampling pattern shown, for example, in FIGS. 4 and 5. Referring particularly to FIG. 4, each point 452 of the rectilinear grid of points shown represents a possible repetition of the pulse sequence used to acquire image data. When such a point is sampled, it is done with a full echo along the frequency encoding direction, in the example provided, normal to the $k_y$-$k_z$ plane. Each point 452 within the central region 400 is sampled in the acquisition. Outside this central region 400 is an annulus composed of radial sectors (402, 404, 406, and 408) that are asymmetrically placed about the $k_y$-$k_z$ origin. Underlying grid points 452 lying within these radial sectors (402, 404, 406, and 408) are sampled, while those points 452 in the annular region, but lying between the radial sectors (402, 404, 406, and 408), are not sampled. If desired for the particular clinical application, signal values at these unsampled points can be estimated from the sampled points using homodyne processing methods.

To acquire time-resolved image data with the foregoing sampling pattern, the entire or substantially the entire set of samples is repetitively sampled; however, the central region 400 is sampled more frequently than the radial sectors (402, 404, 406, and 408) in the peripheral, annular region. A differential sampling rate between the central region 400 and the peripheral region is achieved by grouping the radial sectors (402, 404, 406, and 408) into, for example, four different sets.

The frame rate, or rate at which image reconstruction is performed, is then chosen to match the sampling rate of the central region 400.

Figure 6:
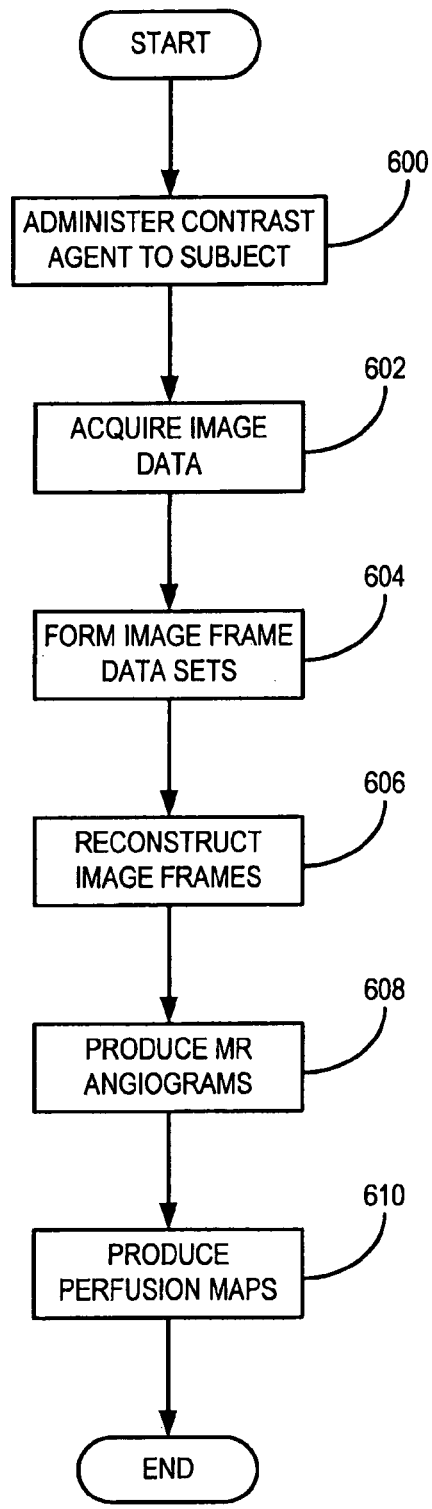
FIG. 6 is a flowchart setting forth the steps of an exemplary method for producing both magnetic resonance angiography ("MRA") images and perfusion images of a subject using the same data acquisition.

Referring now to FIG. 6, a flowchart setting forth the steps of an exemplary method for producing magnetic resonance angiography ("MRA") and perfusion images from data acquired with the same pulse sequence is illustrated. First, a contrast agent is administered to the subject, as indicated at step 600. Exemplary contrast agents include gadolinium based contrast agents such as Gd-DPTA. Next, as indicated at step 602, image data is acquired by directing the MRI system to perform, for example, the pulse sequence shown in FIG. 2. Time-resolved image data is acquired using an appropriate data acquisition timing scheme for the acquisition of image data in accordance with the sampling pattern illustrated in FIG. 4. An exemplary such timing scheme is illustrated in FIG. 7.

Figure 7:
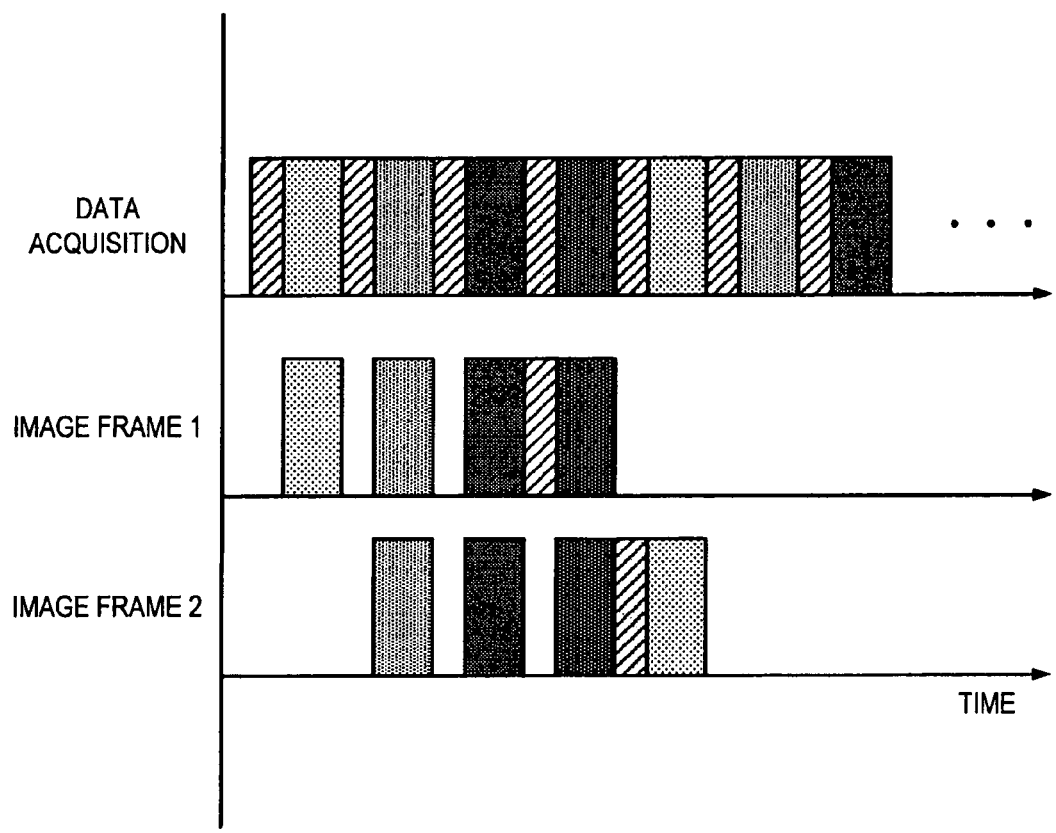
FIG. 7 is a graphic representation of an exemplary timing scheme for acquiring data in accordance with the exemplary method set forth in the flowchart of FIG. 6.

Referring now particularly to FIGS. 4 and 7, the timing scheme starts by sampling k-space at the sample points 452 lying within the central region 400 using an elliptical centric order. After the central region 400 is fully sampled, data acquisition continues immediately to those sample points 452 lying within the lightest shaded radial sectors 402, again using an elliptical centric view order. The radial sectors within each set are selected to span $2\pi$ radians azimuthally in order to impart minimal directional dependence to the point spread function within the y-z plane. After all sampling points 452 within the lightest shaded radial sectors 402 have been sampled the process starts over, and all the sample points 452 within the central region 400 are resampled. Upon completing a second sampling of the central region 400 a different set of radial sectors is sampled. For example, each sample point 452 lying within the set of second lightest radial sectors 404 are sampled following an elliptical centric view order. This process continues for the set of second darkest radial sectors 406 and set of darkest radial sectors 408 as well, at which point the entire data acquisition cycle is repeated.

Referring again to FIG. 6, after image data has been acquired, individual image frame data sets are formed, as indicated at step 604. To sample all of the desired k-space sample points, it is necessary to include samplings of all four sets of radial sectors and at least one sampling of the central region. Because, in the illustrated example, the central region 400 is measured four times more frequently than any one set of radial sectors, there is a choice in which sampling of the central region to use. It is noted that the use of a central region 400 that is followed by a single group of radial sectors, as is shown in FIG. 7, provides a good tradeoff between high spatial resolution and low artifact. In the alternative, other configurations can be employed; however, these configurations may result in a decrease in image quality. For example, the use of a central region 400 at the very end of the sampling causes limited spatial resolution lateral to the leading edge of the advancing contrast bolus, whereas the use of a central region 400 early in the sampling causes artifacts in advance of the contrast bolus. Another alternative, in which multiple samplings of the central region 400 are averaged, blurs the temporal response in the resultant image series.

Exemplary combinations of acquired image data to form separate image frame data sets are illustrated in FIG. 7, in which the four radial sectors and one central region sampling utilized to form an exemplary first and second image frame data set are illustrated. Image frames are subsequently reconstructed from these formed image frame data sets, as indicated at step 606. Since image data is acquired by sampling k-space at Cartesian sampling points, reconstruction occurs in the typical fashion, such as, by Fourier transform. However, other reconstruction methods can similarly be employed. For example, if k-space is undersampled by increasing the Cartesian sampling point spacing and if data acquisition is performed using a receiver coil array, then a parallel reconstruction method such as SENSE can be employed. The time-resolved series of image frames produced in step 606 are subsequently processed in the usual manner to produce MR angiograms, as indicated at step 608.

The reconstructed time series of image frames is also employed to produce maps of perfusion parameters, as indicated at step 610. For example, relative cerebral blood volume ("rCBV") maps can be produced.

As will be described, DCE perfusion methods in accordance with the present invention can utilize a $T_1$-weighted MR acquisition to estimate the leakage of gadolinium contrast material from the intravascular space into the interstitial space, in effect measuring vascular permeability. Accumulation of contrast agent in the interstitial space results in a decrease of the $T_1$ relaxation time related to its concentration. Use of $T_1$-weighted DCE perfusion imaging can substantially reduce the problem with the breakdown of the blood brain barrier (BBB) and permeability, which can plague $T_2^*$-weighted DSC perfusion methods. With DCE methods, tumor enhancement or permeability itself can be used to calculate the rCBV, so permeability effects do not need to be corrected.

As will be described, it is contemplated that the present invention may readily determine physiologic parameters including both first pass kinetic parameters such as cerebral blood volume (CBV), mean transit time (MTT), and cerebral blood flow (CBF), as well as steady state parameters including volume transfer coefficient ($K^{trans}$), which is related to the capillary permeability, endothelial permeability surface area product (PS), extracellular space volume $V_e$, and blood brain barrier rate constant $K_{ep}$, where $K_{ep}=K^{trans}/V_e$.

Figure 8:
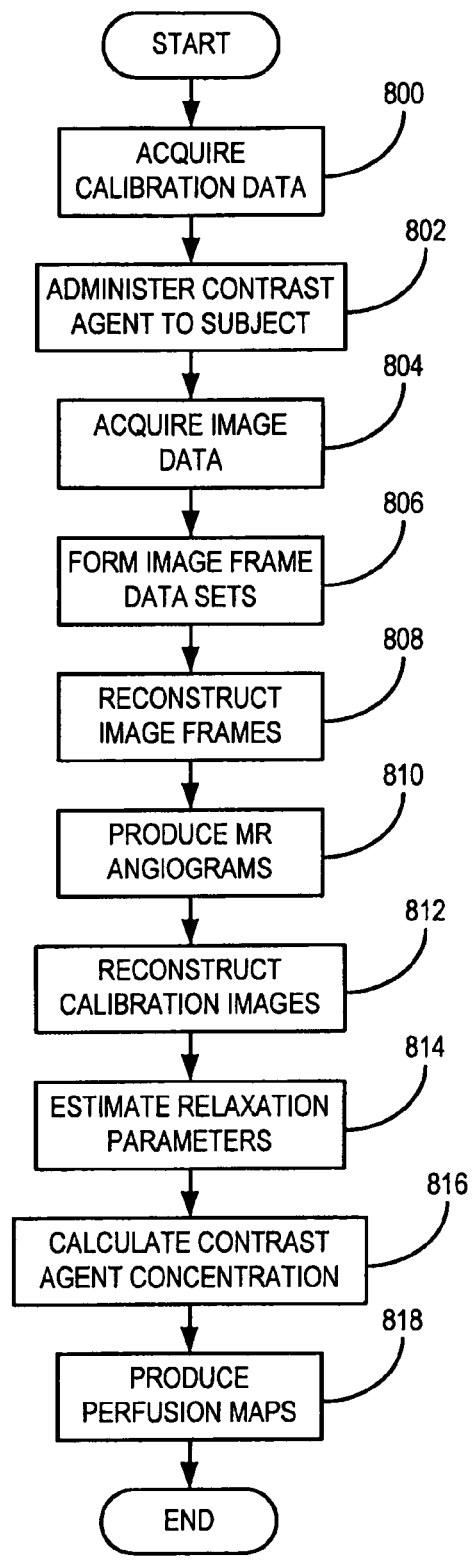
FIG. 8 is a flowchart setting forth the steps of an exemplary method for producing both magnetic resonance angiography ("MRA") images and quantitative perfusion images of a subject using the same data acquisition.

Referring now to FIG. 8, a flowchart setting forth the steps of an exemplary method for producing magnetic resonance angiography ("MRA") and quantitative perfusion images from data acquired with the same pulse sequence is illustrated. The first step in quantitative perfusion estimation is to obtain T1 maps from the volume of interest prior to contrast enhancement. This is accomplished by a calibration scan, as indicated at step 800. Measurement of baseline T1 values on a pixel-by-pixel basis is typically performed by acquiring data that is substantially accurate and of sufficient SNR over a wide range of T1 values, typically from the around 100 milliseconds ("ms") up to around 2000 ms.

After the calibration data has been acquired, a contrast agent is administered to the subject, as indicated at step 802. Subsequently, data acquisition proceeds as described above with respect to step 602, as indicated at step 804. From the acquired image data, image frame data sets are formed next, as indicated at step 806, and discussed above in detail. Image frames are then reconstructed from the image frame data sets, as indicated at step 808. As described above in detail, these image frames are then utilized to produce MR angiograms of the subject, as indicated at step 810.

Pre-contrast, or "calibration," images are then reconstructed from the acquired calibration data, as indicated at step 812. This image reconstruction is performed in the usual sense; however, the particular reconstruction method employed will depend on the manner in which the calibration data is acquired. For example, if the calibration data is acquired using a projection reconstruction type sampling pattern, then projection reconstruction based image reconstruction methods are employed. Likewise, if a Cartesian sampling scheme is utilized, then more traditional Fourier transform based reconstructions are employed.

The reconstructed calibration images are then fitted to a signal model in order to estimate relaxation parameters such as $M_0$ and $R1_0$, as indicated at step 814. There are many ways to perform T1 estimation, such as through use of different inversion times in an inversion recovery pulse sequence. An alternative approach is to use data acquired at different RF flip angles. At least two and up to ten or more gradient echo images with varying flip angles can be used. Various fitting algorithms can then be applied to the acquired data, but ultimately the measured signals are used to estimate $M_0$ and either $T1_0$ or $R1_0 = 1/T1_0$ based on the relationship:

$$s(\alpha) = M_0 \cdot \sin(\alpha) \cdot \left( \frac{1 - e^{-TR \cdot R1_0}}{1 - \cos(\alpha) e^{-TR \cdot R1_0}} \right); \quad \text{Eqn. (4)}$$

where $s(\alpha)$ is the image intensity at a pixel location in the gradient echo image obtained by using the flip angle $\alpha$; $M_0$ is the longitudinal magnetization; TR is the repetition time period of the pulse sequence; and $R1_0$, is the pre-contrast enhanced, or baseline, longitudinal relaxation rate.

One approach is a Levenberg-Marquardt algorithm ("LMA") that interpolates between the Gauss-Newton algorithm ("GNA") and the method of gradient descent. The LMA is more robust than the GNA, which means that in many cases it finds a solution even if it starts very far off the final minimum. On the other hand, for well-behaved functions and reasonable starting parameters, the LMA tends to be a bit slower than the GNA. Another approach is to linearize the Eqn. (4) by fitting $s(\alpha)/\sin(\alpha)$ to $s(\alpha)/\tan(\alpha)$.

The concentration of contrast agent, [CA](t), is calculated next, as indicated at step 816. As the contrast agent passes through a tissue of interest in the subject, it alters the longitudinal relaxation rate in the tissue of interest according to:

$$R1(t) = R1_0 + r_1[CA] \quad \text{Eqn. (5);}$$

where $r_1$ is relaxivity, which defines the change in longitudinal relaxation rate per unit change in contrast agent concentration. Exemplary values of $r_1$ include 4 per seconds per millimolar ($s^{-1}mM^{-1}$) of contrast agent in magnetic field strengths on the order of 1.5 Tesla. The longitudinal relaxation rate can further be modeled according to:

$$R1(t) = \quad \text{Eqn. (6)}$$

$$\left(-\frac{1}{TR}\right)\log\left(\frac{1 - \frac{s(t) - s_0}{M_0 \cdot \sin(\alpha)} + \frac{1 - e^{-TR \cdot R1_0}}{1 - \cos(a) \cdot e^{-TR \cdot R1_0}}}{1 - \cos(\alpha) \cdot \left(\frac{s(t) - s_0}{M_0 \cdot \sin(\alpha)} + \frac{1 - e^{-TR \cdot R1_0}}{1 - \cos(a) \cdot e^{-TR \cdot R1_0}}\right)}\right);$$

where s(t) is the image intensity at a pixel location in the image frame corresponding to time frame, t, and $s_0$ is an image intensity at a corresponding pixel location in the reconstructed pre-contrast images. It, therefore, follows that:

$$[CA](t) = \quad \text{Eqn. (7)}$$

$$-\frac{1}{r_1}\left[\frac{1}{TR} \cdot \log\left(\frac{1 - \frac{s(t) - s_0}{M_0 \cdot \sin(\alpha)} + \frac{1 - e^{-TR \cdot R1_0}}{1 - \cos(a) \cdot e^{-TR \cdot R1_0}}}{1 - \cos(\alpha) \cdot \frac{\left(\frac{s(t) - s_0}{M_0 \cdot \sin(\alpha)} + \frac{1 - e^{-TR \cdot R1_0}}{1 - \cos(a) \cdot e^{-TR \cdot R1_0}}\right)}{}}\right) + R1_0\right];$$

which can be expressed more concisely as:

$$[CA](t) = \frac{1}{r_1} \cdot (R1(t) - R1_0). \quad \text{Eqn. (8)}$$

Next, perfusion parameters are calculated, as indicated at step 818. Exemplary perfusion parameters include both first pass kinetic parameters, such as cerebral blood volume ("CBV"), mean transit time ("MTT"), and cerebral blood flow ("CBF"), as well as steady state parameters including volume transfer coefficient, $K_{trans}$, which is related to capillary permeability, endothelial permeability surface area product ("PS"), extracellular space volume $V_e$, and blood brain barrier rate constant $K_{ep}$, where $K_{ep} = K_{trans}/V_e$.

The rate of accumulation and wash-out of an extracellular contrast medium in the extravascular extracellular space ("EES") is described by the general rate equation:

$$V_e \frac{d}{dt} C_e(t) = K_{trans}(C_P(t) - C_e(t)); \quad \text{Eqn. (9)}$$

where $V_e$ is the volume of the extracellular space per unit volume of tissue; $C_p(t)$ is the concentration of contrast agent in the blood plasma volume, or $V_p$; and $K_{trans}$ is the volume transfer constant between $V_p$ and $V_e$. The concentrations are fit, for example, to the model described by Tofts and Kermode in *Quantitative MRI of the Brain: Measuring Changes Caused by Disease*, John Wiley and Sons, West Sussex, England: 2003, where the tissue concentration is the convolution of the input function with an exponential kernel:

$$C_t(t) = V_p C_p(t) + K_{trans} \int C_p(t') \cdot e^{-\frac{K_{trans}}{V_e}(t-t')} dt'. \quad \text{Eqn. (10)}$$

The first pass bolus dynamics are fit to gamma variate functions on a pixel-by-pixel basis to yield the first pass time concentration curve, C(t). This is done using either a linear least squares estimation of the gamma variate or a Monte-Carlo based non-linear least square technique. The linear least squares approximation is a fast and simple method which is at least semi accurate. The alternative Monte-Carlo-based non-linear least square method is slow and robust and is theoretically guaranteed to converge to an optimal fit.

Cerebral blood volume (CBV) is then determined from the ratio of the sums of the areas under the curves according to:

$$CBV = \frac{\int_{t=t_0}^{t=\infty} C(t)\,dt}{\int_{t=t_0}^{t=\infty} C_{AIF}(t)\,dt}.$$ Eqn. (11)

Mean transit time (MU) can also be determined from the gamma variate fit of first pass data. By the central volume theory, cerebral blood flow (CBF) is given by CBF=CBV/MTT.

Therefore, in light of the foregoing description, a method for acquiring both MRA and perfusion imaging data in the same acquisition that is efficient and requires less time than acquiring the data for both MRA and perfusion separately; requires no timing bolus for time-resolved MRA; provides improved angiographic and perfusion images by mitigating potentially confounding artifacts due to contrast material effects; and utilizes only a single bolus of contrast agent, thereby reducing patient contrast dose, has been provided.

A method referred to as Cartesian acquisition with projection reconstruction-like sampling, or "CAPR," MRA is a time-resolved MRA technique initially developed for MRA. A CAPR acquisition is adapted for simultaneous acquisition of a 4D MR angiogram of a tissue of interest and data which allow estimation of perfusion parameters. Moreover, a SENSE (sensitivity encoding)-accelerated CAPR based technique provides further benefits for perfusion imaging in terms of required criteria. CAPR perfusion has high temporal and spatial resolution, volume coverage, T1 weighting, and adequate SNR. Perfusion parameters may be evaluated on a relative basis, or combined with a measured T1 map for quantitative estimation of perfusion parameters.

With simultaneous acquisition of time-resolved MRA and perfusion using a CAPR pulse sequence, the order of the studies relative to each other is no longer relevant, and optimal time-resolved MRA and perfusion data can be obtained. Performing MRA and perfusion imaging in one sequence also reduces the overall gadolinium dose. Although toxicity of gadolinium is generally non-existent in the absence of renal failure, it remains both prudent and desirable to reduce overall gadolinium administration to the patient.

The CAPR MRA DCE perfusion scan described above requires, in some aspects, approximately 95 seconds for acquisition, and provides both arterial and venous angiographic information useful for diagnosis of both arterial and venous infarctions. No timing bolus is required. The technique is robust, and barring any malfunction of the contrast injection system, it is highly unlikely that the bolus passage of intravascularly administered contrast will be missed. It is expected that a specific stroke imaging protocol including localizer, sagittal and axial morphological imaging, diffusion-weighted imaging, and time-resolved CAPR MRA DCE perfusion can be done in less than 10 minutes. The angiographic and perfusion information could prove highly desirable for dictating therapeutic intervention (e.g. thrombolysis) and for effective follow-up of therapy effects.

The present invention has been described in terms of one or more preferred embodiments, and it should be appreciated that many equivalents, alternatives, variations, and modifications, aside from those expressly stated, are possible and within the scope of the invention.

We claim:

1. A method for producing a magnetic resonance angiography (MRA) image and a perfusion image of a subject with a magnetic resonance imaging (MRI) system, the method comprising the steps of:
   a) acquiring k-space image data from a subject arranged in an MRI system by performing a pulse sequence comprising the steps of:
      i) determining a k-space sampling pattern that divides k-space into a central region and a plurality of radially-extending sectors extending outward from the central region;
      ii) sampling k-space locations within the central region of k-space during a first period and sampling locations within a plurality of the radially-extending sectors during a second period;
      iii) repeating step ii) a plurality of times to acquire time-resolved image data;
   b) forming plurality of image-frame data sets by combining data acquired from the first period with data acquired during the second period;
   c) reconstructing a time series of images from the image-frame data sets; and
   d) producing an MRA image and a perfusion image of the subject from the reconstructed time series of images.

2. The method of claim 1 wherein radially-extending sectors are asymmetrical about the central region.

3. The method of claim 1 wherein step iii) includes sampling k-space locations within the central region and each of the radially-extending sectors during each repetition of step ii).

4. The method of claim 3 wherein step iii) includes sampling k-space locations within the central region more frequently than the radially-extending sectors.

5. The method of claim 1 wherein step ii) includes sampling k-space locations within the central region of k-space using an elliptical centric sampling order.

6. The method of claim 1 wherein step ii) includes sampling k-space locations within the radially-extending sectors of k-space using an elliptical centric sampling order.

7. The method of claim 1 wherein step iii) includes sampling all k-space locations in a first predetermined subset of the radially-extending sectors before sampling k-space locations in a second predetermined subset of the radially extending sectors.

8. The method of claim 7 wherein the first subset of the radially-extending sectors and the second subset of radially-extending sectors are arranged in an alternating fashion radially about the central region of k-space.

9. The method of claim 7 wherein step iii) includes sampling all k-space locations in the second predetermined subset of the radially-extending sectors before sampling k-space locations in a third predetermined subset of the radially extending sectors.

10. The method of claim 1 wherein step i) includes determining the radially-extending sectors to span 2πr radians azimuthally.

11. The method of claim 1 wherein step d) includes determining quantitative perfusion information including at least one of a T1 map, intravascular concentration agent concentration, dynamic contrast enhancement perfusion parameters, and first-pass perfusion parameters.

12. A method for producing a magnetic resonance angiography (MRA) image and a perfusion image of a subject having been administered a contrast agent with a magnetic resonance imaging (MRI) system, the method comprising steps of:
   a) acquiring image data by directing the MRI system to perform a pulse sequence that:
      i) samples k-space points within a central region of k-space during a time frame;

ii) samples k-space points within a plurality of different sets of radial sectors during a respective plurality of additional time frames, the radial sectors extending outward from the central region of k-space to an outer boundary;

iii) repeats steps i) and ii) a plurality of times in order to acquire time-resolved image data;

b) forming a plurality of image frame data sets by combining time-resolved image data acquired by sampling the central region of k-space with time-resolved image data acquired by sampling one of each of the different sets of radial k-space sectors;

c) reconstructing a time series of image frames from the formed plurality of image frame data sets; and d) producing an MRA image and a perfusion image from the reconstructed time series of image frames.

13. The method of claim 12 wherein step iii) includes sampling k-space locations within the central region more frequently than the radial sectors.

14. The method of claim 12 wherein step d) includes determining quantitative perfusion information including at least one of a T1 map, intravascular concentration agent concentration, dynamic contrast enhancement perfusion parameters, and first-pass perfusion parameters.

15. The method of claim 14 further comprising determining at least one of cerebral blood volume (CBV), mean transit time (MU), cerebral blood flow (CBF), volume transfer coefficient, extracellular space volume, and a blood brain barrier rate constant using the reconstructed time series of image frames.

16. A method for producing a magnetic resonance angiography (MRA) image and a perfusion image of a subject with a magnetic resonance imaging (MRI) system, the steps comprising:

a) acquiring pre-contrast image data by directing the MRI system to perform a pulse sequence that samples k-space points within a central region of k-space and k-space points within a plurality of different sets of radial sectors, each radial sector extending outward from the central region of k-space to an outer boundary;

b) following an administration of a contrast agent to the subject, repeating step a) a plurality of times to acquire contrast enhanced image data;

c) forming a plurality of image frame data sets by combining contrast enhanced image data acquired by sampling the central region of k-space with contrast enhanced image data acquired by sampling the different sets of radial k-space sectors;

d) reconstructing a time series of image frames from the plurality of image frame data sets;

e) reconstructing a plurality of pre-contrast images from the pre-contrast image data;

f) determining a concentration of the contrast agent using the reconstructed pre-contrast images; and g) producing an MRA image from the reconstructed time series of image frames and a quantitative perfusion image using the determined concentration of the contrast agent and the reconstructed time series of image frames.

17. The method of claim 16 wherein radial sectors are asymmetrical about the central region of k-space.

18. The method of claim 16 wherein the quantitative perfusion image is formed by estimating relaxation parameters using the pre-contrast images and the plurality of image frame data sets.

19. The method of claim 16 wherein the relaxation parameters include perfusion parameters cerebral blood volume (CBV), mean transit time (MTT), and cerebral blood flow (CBF), volume transfer coefficient, extracellular space volume, and a blood brain barrier rate constant using the plurality of image frame data sets.

20. The method of claim 16 wherein step a) includes sampling k-space locations space using an elliptical centric sampling order.

* * * * *

UNITED STATES PATENT AND TRADEMARK OFFICE
CERTIFICATE OF CORRECTION

PATENT NO. : 9,002,430 B2  
APPLICATION NO. : 13/520302  
DATED : April 7, 2015  
INVENTOR(S) : Stephen J. Riederer, Norbert G. Campeau and Clifton R. Haider Page 1 of 1

It is certified that error appears in the above-identified patent and that said Letters Patent is hereby corrected as shown below:

In the Claims

Column 17, line 27 - "(MU)" should be --(MTT)--

Signed and Sealed this
Twenty-first Day of July, 2015

Michelle K. Lee
*Director of the United States Patent and Trademark Office*